(12) United States Patent
Jeon et al.

(10) Patent No.: US 11,026,876 B2
(45) Date of Patent: Jun. 8, 2021

(54) COMPOSITION FOR IMPROVING SKIN CONDITION COMPRISING CHEMOKINES

(71) Applicant: TEGO SCIENCE INC., Seoul (KR)

(72) Inventors: Saewha Jeon, Seoul (KR); Yun Hee Kim, Seoul (KR); Jik Hyon Han, Seoul (KR); Hyun Ah Moon, Seoul (KR)

(73) Assignee: Tego Science Inc., Seoul (KR)

( * ) Notice: Subject to any disclaimer, the term of this patent is extended or adjusted under 35 U.S.C. 154(b) by 215 days.

(21) Appl. No.: 16/324,580

(22) PCT Filed: Jul. 28, 2017

(86) PCT No.: PCT/KR2017/008169
§ 371 (c)(1),
(2) Date: Feb. 11, 2019

(87) PCT Pub. No.: WO2018/030688
PCT Pub. Date: Feb. 15, 2018

(65) Prior Publication Data
US 2019/0175480 A1    Jun. 13, 2019

(30) Foreign Application Priority Data
Aug. 10, 2016  (KR) .................. 10-2016-0101765

(51) Int. Cl.
| | | |
|---|---|---|
| *A61K 8/64* | (2006.01) | |
| *A61K 8/65* | (2006.01) | |
| *A61K 8/73* | (2006.01) | |
| *A61K 38/19* | (2006.01) | |
| *A61K 47/36* | (2006.01) | |
| *A61Q 19/02* | (2006.01) | |
| *A61Q 19/08* | (2006.01) | |
| *C07K 14/52* | (2006.01) | |
| *A61Q 19/00* | (2006.01) | |

(52) U.S. Cl.
CPC .................. *A61K 8/64* (2013.01); *A61K 8/65* (2013.01); *A61K 8/733* (2013.01); *A61K 8/735* (2013.01); *A61K 38/195* (2013.01); *A61K 47/36* (2013.01); *A61Q 19/00* (2013.01); *A61Q 19/007* (2013.01); *A61Q 19/02* (2013.01); *A61Q 19/08* (2013.01); *C07K 14/521* (2013.01); *A61K 2800/5922* (2013.01)

(58) Field of Classification Search
CPC .... A61K 2300/00; A61K 38/19; A61K 38/00; A61K 8/00; A61K 8/02; A61K 8/18; A61K 8/64; A61K 8/65; A61K 8/731; A61K 8/733; A61K 38/195; A61K 47/36; C07K 14/521; C07K 14/52
See application file for complete search history.

(56) References Cited

U.S. PATENT DOCUMENTS

2013/0344119 A1   12/2013   Lee et al.

FOREIGN PATENT DOCUMENTS

| CN | 105250994 | 1/2016 |
|---|---|---|
| JP | 2015-531380 | 11/2015 |
| KR | 10-2010-0032099 | 3/2010 |
| KR | 10-2011-0057222 | 5/2011 |
| KR | 10-1698447 | 1/2017 |
| WO | WO 2018/030688 | 2/2018 |

OTHER PUBLICATIONS

Brovold et al. Naturally-derived biomaterials for tissue engineering applications. Adv Exp Med Biol 1077: 421-449, 2018.*
Gunn et al. A B-cell homing chemokine made in lymphoid follicles activates Burkitt's lymphoma receptor-1. Naure 391(6669): 799-803, 1998.*
Mitura et al. Biopolymers for hydrogels in cosmetics: review. J Mat Sci Mat Med 31: 50, 2020 (14 total pages).*
Mogosanu et al. Natural and synthetic polymers for wounds and burns dressing. Int J Pharmaceutics 463: 127-136, 2014.*
Vicari et al. TECK: a novel CC chemokine specifically expressed by thymic dendritic cells and potentially involved in T cell development.*
International Search Report dated Oct. 30, 2017 From the International Searching Authority Re. Application No. PCT/KR2017/008169 and Its Translation Into English. (5 Pages).

* cited by examiner

*Primary Examiner* — Bridget E Bunner

(57) ABSTRACT

The present invention relates to a composition for skin improvement containing at least one chemokine selected from the group consisting of B lymphocyte chemoattractant (BLC), also known as C-X-C motif ligand 13 (CXCL13), and thymus-expressed chemokine (TECK), also known as C-C motif ligand 25 (CCL25), as an active ingredient. Since the BLC (CXCL13) and TECK (CCL25) of the present invention increase the expression of proliferation marker Ki-67 and collagen IV, which are proteins concerning skin regeneration and skin elasticity, and exhibit excellent melanin-reducing and wound-healing effects and the ability to induce chemotaxis of keratinocytes, they can be applied in a cosmetic composition for skin improvement.

9 Claims, 6 Drawing Sheets
(4 of 6 Drawing Sheet(s) Filed in Color)

Negative control

AL+TECK

AL+BLC

US 11,026,876 B2

COMPOSITION FOR IMPROVING SKIN CONDITION COMPRISING CHEMOKINES

RELATED APPLICATIONS

This application is a National Phase of PCT Patent Application No. PCT/KR2017/008169 having International filing date of Jul. 28, 2017, which claims the benefit of priority of Korean Patent Application No. 10-2016-0101765 filed on Aug. 10, 2016. The contents of the above applications are all incorporated by reference as if fully set forth herein in their entirety.

FIELD AND BACKGROUND OF THE INVENTION

The present invention relates to a composition for skin improvement containing at least one chemokine selected from the group consisting of B lymphocyte chemoattractant (BLC), also known as B cell-attracting chemokine 1 (BCA-1) or C-X-C motif ligand 13 (CXCL13), and thymus-expressed chemokine (TECK), also known as C-C motif ligand 25 (CCL25), as an active ingredient.

Skin is a tissue that consists of three layers such as the epidermis, the dermis, and the subcutis and functions as a barrier of a living body by absorbing external stress caused by physical stress and chemical changes, thereby maintaining the internal environment and providing protection for the body.

The epidermis is the outermost layer of skin, and 95% thereof is made of keratinocytes. Keratinocytes play a protective role against bacteria and chemicals penetrating the skin and are involved in an inflammatory reaction and immune response of the skin by secreting various cytokines. Also, keratinocytes maintain skin elasticity and promote skin regeneration and wound healing by inducing the synthesis of collagen IV, laminin, and the like through proliferation and migration.

Accordingly, there has been a demand for a material capable of maintaining skin elasticity and promoting skin regeneration and wound healing by inducing the proliferation and migration of keratinocytes and the synthesis and secretion of collagen IV when the physiological activity of keratinocytes has been reduced due to skin aging, wounds, and lesions caused by various causes.

The inventors of the present invention have discovered that a chemokine such as B lymphocyte chemoattractant (BLC) (also known as B cell-attracting chemokine 1 (BCA-1) or C-X-C motif ligand 13 (CXCL13)) or thymus-expressed chemokine (TECK) (also known as C-C motif ligand 25 (CCL25)) has the ability to induce chemotaxis of keratinocytes, increases the expression of a protein concerning skin regeneration and skin elasticity, and exhibits excellent skin whitening and wound-healing activities, developed a cosmetic composition for skin improvement containing the chemokine as an active ingredient, and thereby completed the present invention.

SUMMARY OF THE INVENTION

One objective of the present invention is to provide a cosmetic composition for skin improvement containing at least one chemokine selected from the group consisting of B lymphocyte chemoattractant (BLC) (also known as C-X-C motif ligand 13 (CXCL13)) and thymus-expressed chemokine (TECK) (also known as C-C motif ligand 25 (CCL25)) as an active ingredient.

Another objective of the present invention is to provide a method for skin improvement that includes applying the cosmetic composition containing at least one active ingredient selected from the group consisting of BLC (CXCL13) and TECK (CCL25) to the skin for skin improvement.

Still another objective of the present invention is to provide use of BLC (CXCL13) and TECK (CCL25) for skin improvement.

The present invention provides a cosmetic composition for skin improvement containing at least one chemokine selected from the group consisting of BLC (CXCL13) and TECK (CCL25) as an active ingredient.

Also, the present invention provides a method for skin improvement that includes applying the cosmetic composition containing at least one active ingredient selected from the group consisting of BLC (CXCL13) and TECK (CCL25) to the skin for skin improvement.

In addition, the present invention provides use of BLC (CXCL13) and TECK (CCL25) for skin improvement.

Since BLC (also known as BCA-1 or CXCL13) and TECK (CCL25) according to the present invention increase the expression of proliferation marker Ki-67 and collagen IV which are proteins concerning skin regeneration and skin elasticity among keratinocyte-derived cell-secreted substances, have excellent melanin-reducing and wound-healing effects, and exhibit the ability to induce chemotaxis of keratinocytes, they can be applied in a cosmetic composition for skin improvement.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

The above and other objects, features, and advantages of the present invention will become more apparent to those of ordinary skill in the art by describing in detail exemplary embodiments thereof with reference to the accompanying drawings, in which.

DESCRIPTION OF SPECIFIC EMBODIMENTS OF THE INVENTION

Hereinafter, the present invention will be described in greater detail with reference to examples. However, these examples are for illustrative purposes only, and the scope of the present invention is not limited to these examples. The examples of the present invention are provided to fully explain the invention for those skilled in the art.

<Example 1> Culture of Keratinocytes

The keratinocytes isolated from normal skin tissue were cocultured with 3T3 feeder cells in a DMEM/F12 medium (Invitrogen™, Thermo Fisher Scientific Inc., United States) containing 10% fetal bovine serum (FBS) in a humid environment of 37° C. and 10% $CO_2$. When the cultured cells grew by 70 to 80%, the 3T3 feeder cells were removed and only the keratinocytes were isolated using trypsin-EDTA.

<Experimental Example 1> Evaluation of Chemotaxis of Keratinocytes

To evaluate chemotaxis of keratinocytes in response to BLC (CXCL13) or TECK (CCL25), cells were cultured using a Transwell® insert (Falcon®, Corning Incorporated, United States) with an opening size of 8 μm, and the number of cells migrated passing through micropores in the insert toward the chemokine were counted. Specifically, the lower chamber of the insert was treated with a chemokine (100 or 500 ng/ml BLC (CXCL13) or 100 or 500 ng/ml TECK (CCL25)), and then cells were placed in wells of the insert in a ratio of $1\times10^4$ cells per well. After cell incubation in a humid environment of 37° C. and 10% $CO_2$ for six hours, the insert membrane was stained with hematoxylin, and then the number of migrated cells were counted.

Figure 1:
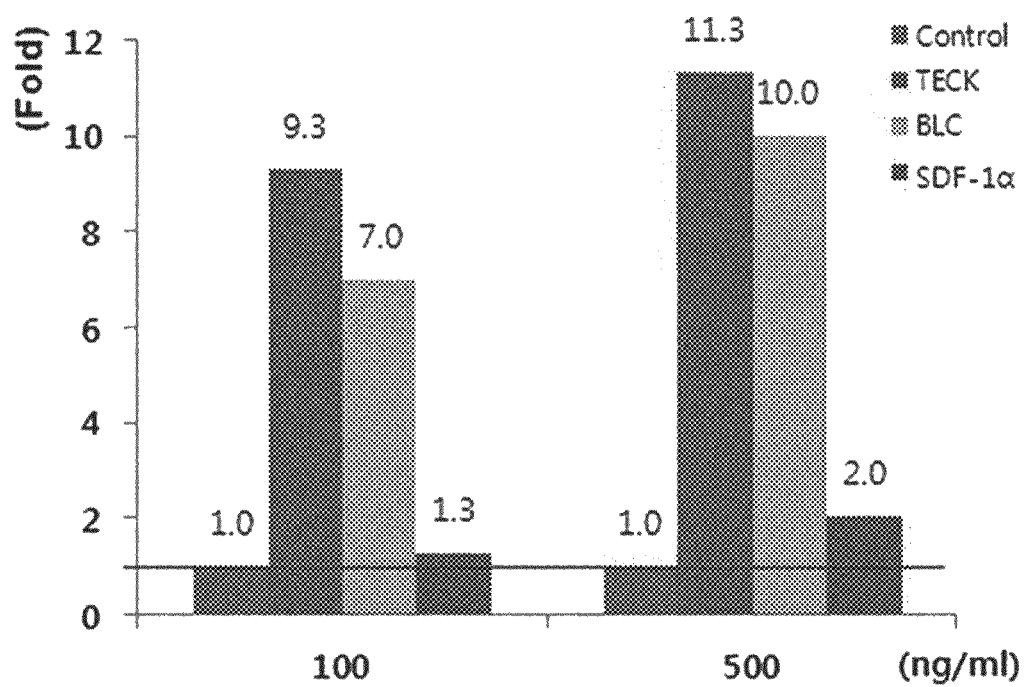
FIG. 1 shows the results of evaluating the ability of B lymphocyte chemoattractant (BLC) (also known as C-X-C motif ligand 13 (CXCL13)) or thymus-expressed chemokine (TECK) (also known as C-C motif ligand 25 (CCL25)) to induce chemotaxis of keratinocytes, wherein "Control" refers to a negative control, which is an untreated group, and "SDF-1α" refers to a positive control.

The results show that migration of keratinocytes was increased by BLC (CXCL13) or TECK (CCL25) compared to the negative control, which was a group not treated with a chemokine, and that at least five times more keratinocytes migrated by BLC (CXCL13) or TECK (CCL25) than by stromal cell-derived factor-1α (SDF-1α), which is a cytokine (FIG. 1).

<Experimental Example 2> Evaluation of Wound-Healing Effect of Chemokine Using Three-Dimensional Skin Culture Model A Neoderm®-ED (TEGO Science, Korea) consisting of the dermis including collagen and fibroblasts and the epidermis including keratinocytes was prepared. A wound was induced on the Neoderm®-ED using a 4-mm biopsy punch, and the wound was treated with a 500 ng/ml chemokine (BLC (CXCL13) or TECK (CCL25)) and incubated in a humid environment of 37° C. and 10% $CO_2$ for five days. The cultured Neoderm®-ED tissue was separated from insert wells and stained with hematoxylin and eosin (H&E staining). The stained tissue was placed on a glass slide and photographed under a microscope. The obtained images were analyzed using Image-Pro™ image analysis software (Media Cybernetics, Inc., United States) to measure a length of re-epithelialization of the wound.

Figure 2:
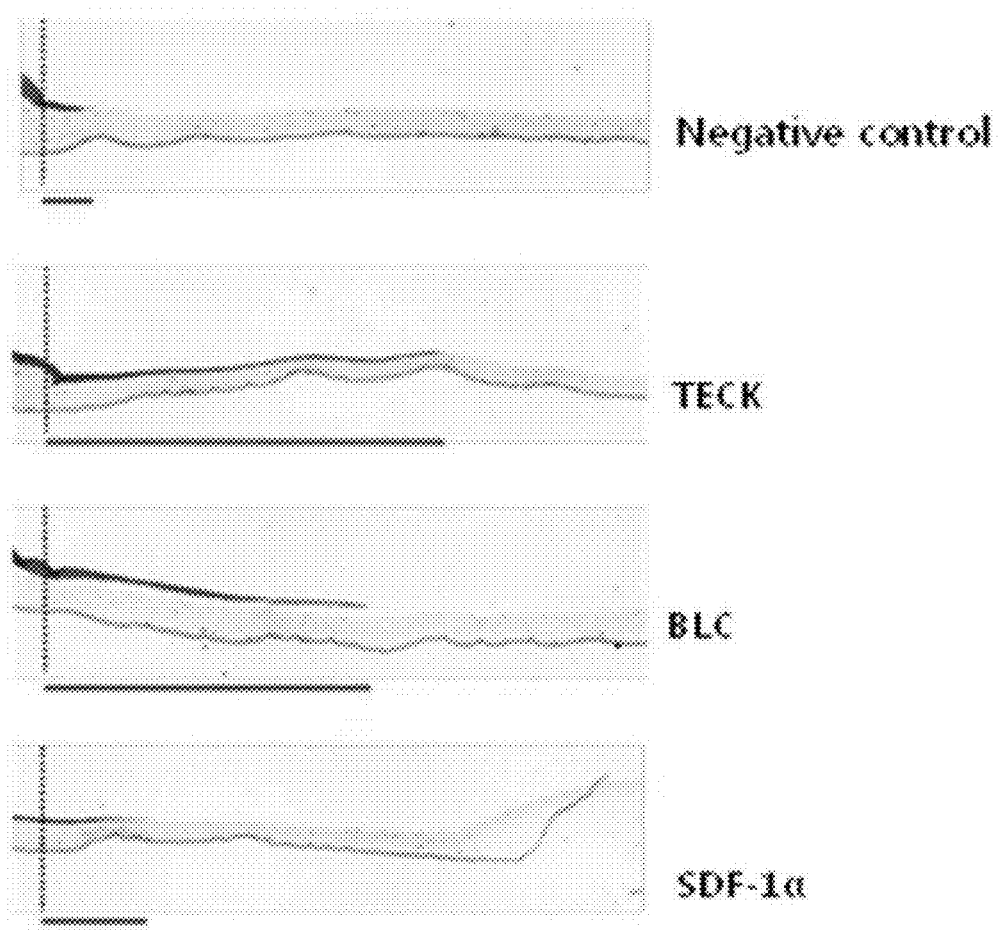
FIG. 2 shows the results of treating a wound formed in a three-dimensional skin culture model with BLC (CXCL13) or TECK (CCL25) to induce re-epithelialization, wherein "Negative control" refers to an untreated group and "SDF-1α" refers to a positive control.

The results show that treatment with BLC (CXCL13) or TECK (CCL25) resulted in a significantly greater length of re-epithelialization compared to the negative control (untreated group), and that at least a three times greater length of re-epithelialization resulted by treatment with BLC (CXCL13) or TECK (CCL25) than by treatment with SDF-1α (FIG. 2).

<Experimental Example 3> Evaluation of Skin Regeneration, Skin Elasticity Improvement, and Skin Whitening Effects of Chemokine Using Three-Dimensional Skin Culture Model To evaluate the effects of skin regeneration and skin elasticity improvement, a Neoderm®-ED was treated with a 100 ng/ml chemokine (BLC (CXCL13) or TECK (CCL25)) and incubated in a humid environment of 37° C. and 10% $CO_2$ for 48 hours. Then, the Neoderm®-ED was reacted with primary antibodies that bind to markers (i.e., proliferation marker Ki-67 and collagen IV) used to confirm the ability to induce skin regeneration and skin elasticity and then with secondary antibodies labeled with a fluorescent substance. Cell nuclei were stained with 4',6-diamidino-2-phenylindole (DAPI).

To evaluate skin whitening effects, a Neoderm®-ME (TEGO Science, Korea) was treated with a 500 ng/ml chemokine (BLC (CXCL13) or TECK (CCL25)) and incubated in a humid environment of 37° C. and 10% $CO_2$ for 48 hours. A lysis buffer was added and reacted with the Neoderm®-ME at 95° C. for 45 minutes to cause the tissue to be disintegrated and elute melanin from the tissue. The absorbance of the eluate was measured at 405 nm, and the eluted melanin was quantified using a melanin standard curve (1.56 to 100 μg/ml).

Figure 3:
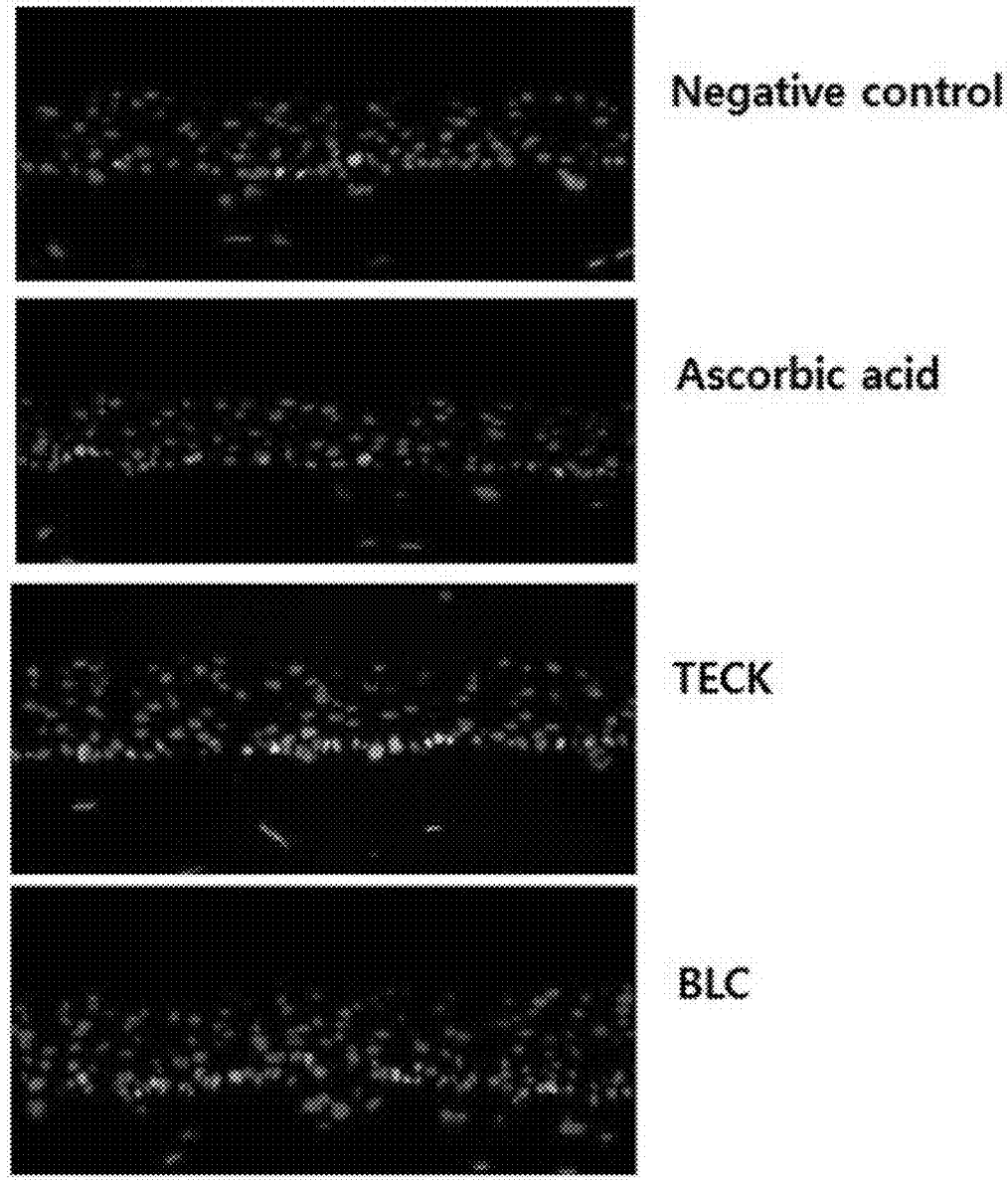
FIG. 3 shows effects of treatment with BLC (CXCL13) or TECK (CCL25) on the expression of the Ki-67 marker, wherein "Negative control" refers to an untreated group and "Ascorbic acid" refers to a positive control.
Figure 4:
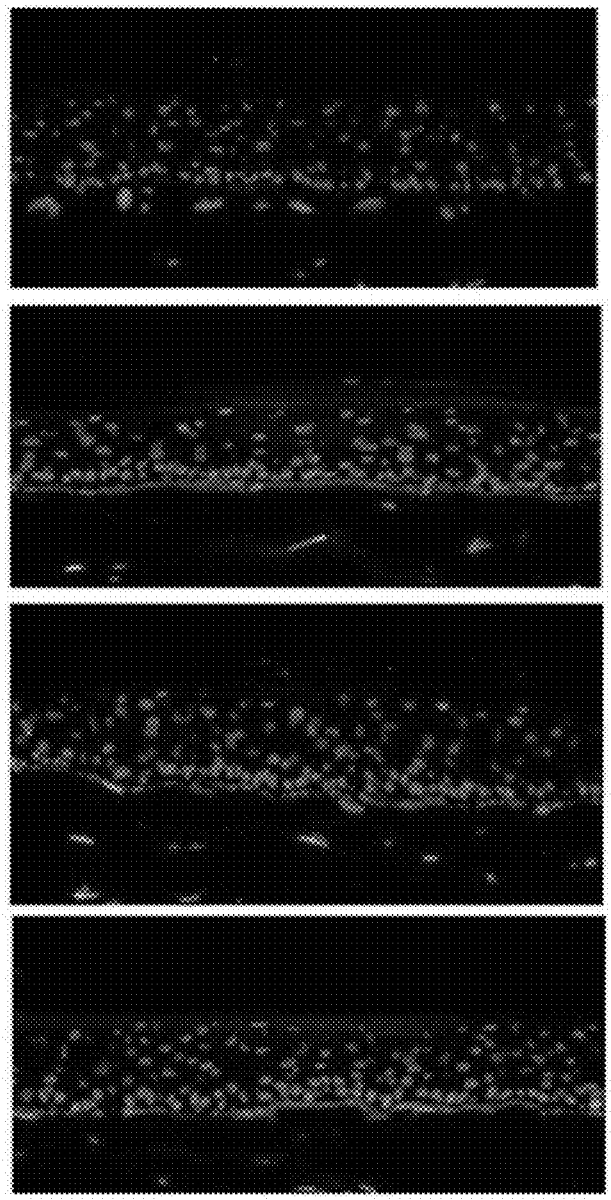
FIG. 4 shows effects of treatment with BLC (CXCL13) or TECK (CCL25) on the expression of collagen IV marker, wherein "Negative control" refers to an untreated group and "Ascorbic acid" refers to a positive control.
Figure 5:
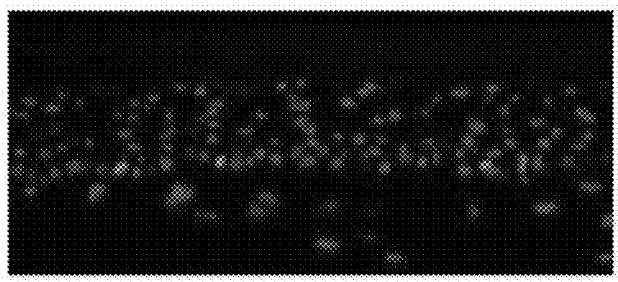
FIG. 5 shows effects of treatment with a BLC (CXCL13) or TECK (CCL25) in alginate (AL) on the expression of the Ki-67 marker, wherein "Negative control" refers to an untreated group.
Figure 5:
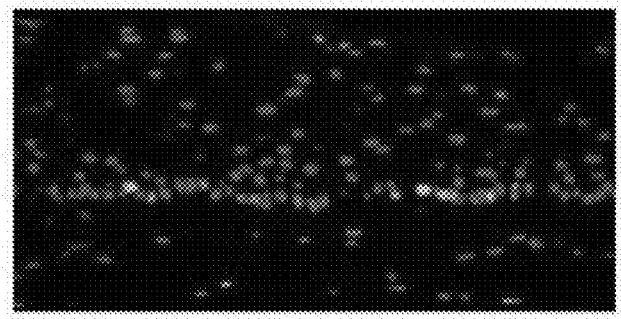
Figure 5:
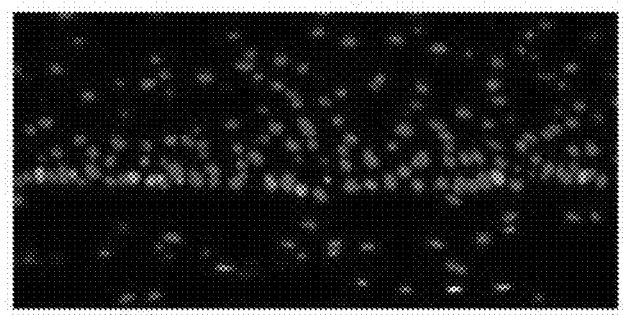

The results show that the expression of each marker was increased by BLC (CXCL13) or TECK (CCL25) compared to the negative control (untreated group), and that the expression of both proliferation marker Ki-67 (FIGS. 3 and 5) and collagen IV (FIG. 4) was increased more significantly by BLC (CXCL13) or TECK (CCL25) than by SDF-1α, which is a cytokine.

Figure 6:
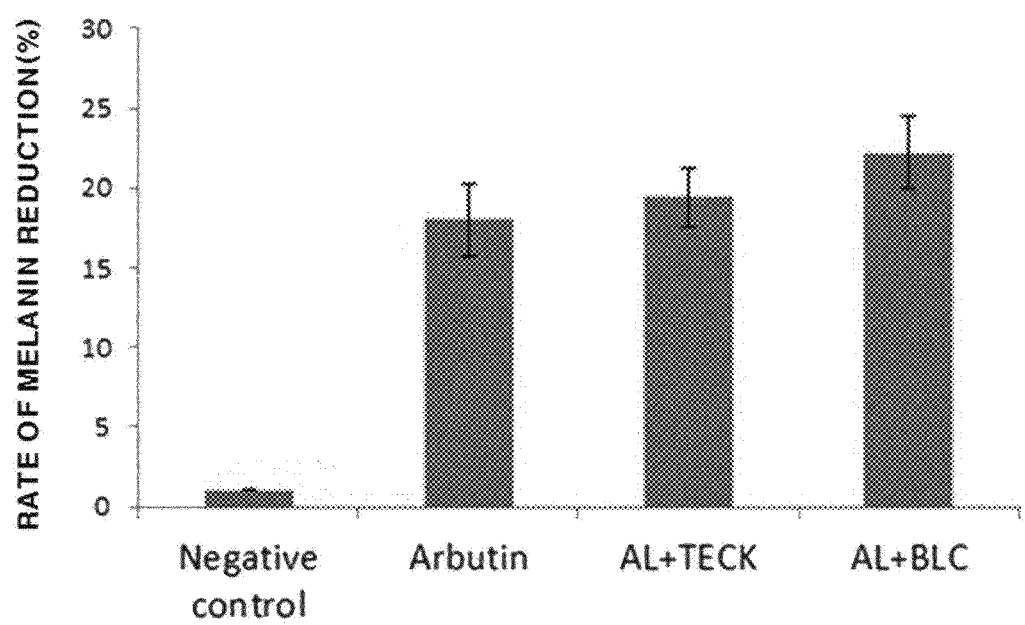
FIG. 6 shows effects of treatment with a BLC (CXCL13) or TECK (CCL25) in alginate (AL) on the rate of melanin reduction, wherein "Negative control" refers to an untreated group and "Arbutin" refers to a positive control.

In addition, it can be seen that the rate of melanin reduction caused by BLC (CXCL13) or TECK (CCL25) was higher by 20 percentage points or more compared to the negative control (untreated group) (FIG. 6).

<Experimental Example 4> Evaluation of Skin Elasticity Improvement Effects of Cosmetic Compositions Containing Chemokine The skin elasticity improvement effects of cosmetic compositions of Preparation Examples 1 to 12 and Comparative Examples 1 to 4 were evaluated using a cutometer (Courage+Khazaka electronic GmbH, Germany) capable of measuring skin elasticity based on changes in skin morphology upon application of sound pressure to a skin surface. Specifically, the evaluation was performed by asking fifty healthy female individuals aged from 35 to 55 to apply the cosmetic compositions of Preparation Examples 1 to 12 and Comparative Examples 1 to 4 to either side of their facial area twice a day for two months. Net skin elasticity (R5) was measured twice at the same sites on the facial area of each participant by using the cutometer, once prior to the experiment and the second time immediately after the experiment. The rate of increase in skin elasticity determined by the cutometer was calculated as the average of the ratio of R5 after use of each cosmetic composition to R5 prior to use of the cosmetic composition.

The results of measuring skin elasticity improvement effects of each cosmetic composition are provided in Table 1 below.

TABLE 1

| Cosmetic composition | Rate of increase in skin elasticity (R5) (%) |
|---|---|
| Preparation Example 1 | 35.1 |
| Preparation Example 2 | 36.5 |
| Preparation Example 3 | 38.9 |
| Comparative Example 1 | 2.0 |
| Preparation Example 4 | 39.7 |
| Preparation Example 5 | 42.3 |
| Preparation Example 6 | 43.5 |
| Comparative Example 2 | 2.5 |
| Preparation Example 7 | 41.1 |
| Preparation Example 8 | 43.4 |
| Preparation Example 9 | 44.9 |
| Comparative Example 3 | 3.3 |
| Preparation Example 10 | 43.5 |
| Preparation Example 11 | 45.8 |
| Preparation Example 12 | 47.1 |
| Comparative Example 4 | 3.9 |

The skin elasticity measurement results show that the cosmetic compositions of Preparation Examples 1 to 12 which contain BLC (CXCL13) and/or TECK (CCL25) according to the present invention had greater skin elasticity improvement effects compared to the cosmetic compositions of Comparative Examples 1 to 4 which do not contain BLC (CXCL13) or TECK (CCL25).

<Experimental Example 5> Evaluation of Skin Elasticity Improvement Efficacy of Cosmetic Compositions Containing Chemokine The skin elasticity improvement efficacy of cosmetic compositions prepared according to Preparation Examples 10 to 12 and Comparative Example 4 was evaluated. Specifically, the efficacy was tested on a total of 45 participants (men and women) aged between 30 and 60 (i.e., 15 participants in their 30s, 15 participants in their 40s, 15 participants in their 50s or 60s) who were divided into three groups such that each group had five participants in their 30s, five participants in their 40s, and five participants in their 50s or 60s. All participants were asked to continuously apply various cosmetic compositions to heavily wrinkled portions in a facial area once a day for two weeks: participants in group 1 were asked to apply the cosmetic composition of Comparative Example 4 (control group) to a left corner of the lips or the corner of a left eye and the cosmetic composition of Preparation Example 10 (experimental group) to a right corner of the lips or the corner of a right eye; participants in group 2 were asked to apply the cosmetic composition of Comparative Example 4 (control group) to the same sites on the left side of the facial area and the cosmetic composition of Preparation Example 11 (experimental group) to the same sites on the right side of the facial area; and participants in group 3 were asked to apply the cosmetic composition of Comparative Example 4 (control group) to the same sites on the left side of the facial area and the cosmetic composition of Preparation Example 12 (experimental group) to the same sites on the right side of the facial area. Skin elasticity improvement effects were evaluated based on the flattening of wrinkles around eyes or lips, and skin elasticity maintenance effects were evaluated in the same manner and, in addition, by counting the number of days during which skin elasticity was maintained. Skin irritation was evaluated in terms of itchy and stinging sensations, the occurrence of erythema, and the like. Each evaluation item was rated based on a maximum of five points: 5 (excellent), 4 (good), 3 (average), 2 (poor), and 1 (very bad).

The results of measuring skin regeneration and skin elasticity improvement efficacy of each cosmetic composition are provided in Table 2 below.

TABLE 2

| | | Evaluation items | | | | | | | | | |
|---|---|---|---|---|---|---|---|---|---|---|---|
| | | Skin elasticity improvement | | | | Skin elasticity maintenance | | | | Skin irritation reduction | | |
| Participant No. (sorted by age) | | Preparation Example 10 | Preparation Example 11 | Preparation Example 12 | Comparative Example 4 | Preparation Example 10 | Preparation Example 11 | Preparation Example 12 | Comparative Example 4 | Preparation Example 10 | Preparation Example 11 | Preparation Example 12 |
| 30s | 1 | 4 | | | 3 | 5 | | | 3 | 5 | | |
| | 2 | 3 | | | 3 | 3 | | | 3 | 5 | | |
| | 3 | 5 | | | 4 | 4 | | | 2 | 5 | | |
| | 4 | 3 | | | 2 | 4 | | | 2 | 4 | | |
| | 5 | 4 | | | 3 | 4 | | | 3 | 4 | | |
| | 6 | | 5 | | 2 | | 4 | | 2 | | 4 | |
| | 7 | | 4 | | 2 | | 4 | | 3 | | 5 | |
| | 8 | | 5 | | 3 | | 5 | | 4 | | 5 | |
| | 9 | | 4 | | 4 | | 3 | | 2 | | 4 | |
| | 10 | | 4 | | 4 | | 4 | | 3 | | 3 | |
| | 11 | | | 4 | 3 | | | 4 | 4 | | | 4 |
| | 12 | | | 5 | 3 | | | 5 | 3 | | | 5 |
| | 13 | | | 5 | 2 | | | 4 | 3 | | | 4 |
| | 14 | | | 5 | 3 | | | 4 | 2 | | | 4 |
| | 15 | | | 4 | 3 | | | 5 | 2 | | | 4 |
| 40s | 11 | 3 | | | 3 | 3 | | | 2 | 3 | | |
| | 12 | 4 | | | 3 | 4 | | | 4 | 4 | | |
| | 13 | 4 | | | 2 | 5 | | | 4 | 5 | | |
| | 14 | 5 | | | 3 | 5 | | | 3 | 5 | | |
| | 15 | 5 | | | 4 | 4 | | | 3 | 4 | | |
| | 16 | | 4 | | 4 | | 5 | | 3 | | 5 | |
| | 17 | | 5 | | 3 | | 5 | | 3 | | 4 | |

TABLE 2-continued

| | | Evaluation items | | | | | | | | | | |
|---|---|---|---|---|---|---|---|---|---|---|---|---|
| | | Skin elasticity improvement | | | | Skin elasticity maintenance | | | | Skin irritation reduction | | |
| Participant No. (sorted by age) | | Preparation Example 10 | Preparation Example 11 | Preparation Example 12 | Comparative Example 4 | Preparation Example 10 | Preparation Example 11 | Preparation Example 12 | Comparative Example 4 | Preparation Example 10 | Preparation Example 11 | Preparation Example 12 |
| | 18 | | 4 | | 3 | | 4 | | 4 | 4 | | |
| | 19 | | 5 | | 4 | | 4 | | 3 | 3 | | |
| | 20 | | 5 | | 3 | | 4 | | 3 | 5 | | |
| | 21 | | | 5 | 3 | | | 5 | 3 | | | 4 |
| | 22 | | | 5 | 4 | | 4 | | 3 | | | 5 |
| | 23 | | | 4 | 2 | | | 5 | 4 | | | 5 |
| | 24 | | | 4 | 3 | | | 5 | 2 | | | 4 |
| | 25 | | | 5 | 3 | | | 4 | 3 | | | 3 |
| 50s and 60s | 21 | 4 | | | 3 | 3 | | | 2 | 4 | | |
| | 22 | 4 | | | 3 | 3 | | | 2 | 4 | | |
| | 23 | 3 | | | 3 | 4 | | | 2 | 4 | | |
| | 24 | 3 | | | 3 | 4 | | | 3 | 5 | | |
| | 25 | 4 | | | 4 | 5 | | | 3 | 4 | | |
| | 26 | | 3 | | 2 | | 4 | | 3 | | 5 | |
| | 27 | | 4 | | 3 | | 4 | | 2 | | 4 | |
| | 28 | | 4 | | 3 | | 5 | | 4 | | 4 | |
| | 29 | | 4 | | 2 | | 3 | | 3 | | 4 | |
| | 30 | | 4 | | 2 | | 3 | | 2 | | 3 | |
| | 31 | | | 4 | 3 | | | 4 | 3 | | | 5 |
| | 32 | | | 4 | 3 | | | 5 | 3 | | | 4 |
| | 33 | | | 5 | 3 | | | 5 | 4 | | | 4 |
| | 34 | | | 4 | 4 | | | 4 | 3 | | | 4 |
| | 35 | | | 3 | 3 | | | 3 | 3 | | | 5 |
| | Average | 3.9 | 4.3 | 4.4 | 3 | 4 | 4.1 | 4.4 | 2.9 | 4.3 | 4.1 | 4.3 |

The results show that the cosmetic compositions of Preparation Examples 10 to 12 which contain BLC (CXCL13) and/or TECK (CCL25) according to the present invention as an active ingredient(s) are effective in improving wrinkles and maintaining skin elasticity compared to the cosmetic composition of Comparative Example 4.

<Preparation Examples 1 to 3 and Comparative Example 1> Preparation of Skin Lotions Containing Chemokine Skin lotions of Preparation Example 1, Preparation Example 2, and Preparation Example 3, respectively containing BLC (CXCL13), TECK (CCL25), and both BLC (CXCL13) and TECK (CCL25) as an active ingredient(s) and other ingredients at concentrations shown in the following Table 3, were prepared. Also, a skin lotion of Comparative Example 1 containing ingredients at concentrations shown in the following Table 3 but no BLC (CXCL13) or TECK (CCL25) as an active ingredient was prepared.

TABLE 3

| Ingredients | Preparation Example 1: BLC (CXCL13) (500 ng/ml) (wt %) | Preparation Example 2: TECK (CCL25) (500 ng/ml) (wt %) | Preparation Example 3: BLC (CXCL13) + TECK (CCL25) (500 ng/ml) (wt %) | Comparative Example 1 (wt %) |
|---|---|---|---|---|
| BLC (CXCL13)/ TECK (CCL25)/ BLC (CXCL13) + TECK (CCL25) | 0.01 | 0.01 | 0.01 | — |
| Amino acid stock | 0.1 | 0.1 | 0.1 | 0.1 |
| Mineral mixture | 0.0007 | 0.0007 | 0.0007 | 0.0007 |
| Purified water | Remainder | Remainder | Remainder | Remainder |

<Preparation Examples 4 to 6 and Comparative Example 2> Preparation of Serums Containing Chemokine Serums of Preparation Example 4, Preparation Example 5, and Preparation Example 6, respectively containing BLC (CXCL13), TECK (CCL25), and both BLC (CXCL13) and TECK (CCL25) as an active ingredient(s) and other ingredients at concentrations shown in the following Table 4, were prepared. Also, a serum of Comparative Example 2 containing ingredients at concentrations shown in the following Table 4 but no BLC (CXCL13) or TECK (CCL25) as an active ingredient was prepared.

TABLE 4

| Ingredients | Preparation Example 4: BLC (CXCL13) (500 ng/ml) (wt %) | Preparation Example 5: TECK (CCL25) (500 ng/ml) (wt %) | Preparation Example 6: BLC (CXCL13) + TECK (CCL25) (500 ng/ml) (wt %) | Comparative Example 2 (wt %) |
|---|---|---|---|---|
| BLC (CXCL13)/ TECK (CCL25)/ BLC (CXCL13) + TECK (CCL25) | 0.01 | 0.01 | 0.01 | — |
| Amino acid stock | 0.05 | 0.05 | 0.05 | 0.05 |
| Mineral mixture | 0.0007 | 0.0007 | 0.0007 | 0.0007 |
| Glycerol | 5 | 5 | 5 | 5 |
| 1,3-Butylene glycol | 10 | 10 | 10 | 10 |
| Carbopol ® 940 | 0.3 | 0.3 | 0.3 | 0.3 |
| Purified water | Remainder | Remainder | Remainder | Remainder |

<Preparation Examples 7 to 9 and Comparative Example 3> Preparation of Emulsions Containing Chemokine Emulsions of Preparation Example 7, Preparation Example 8, and Preparation Example 9, respectively containing BLC (CXCL13), TECK (CCL25), and both BLC (CXCL13) and TECK (CCL25) as an active ingredient(s) and other ingredients at concentrations shown in the following Table 5, were prepared. Also, an emulsion of Comparative Example 3 containing ingredients at concentrations shown in the following Table 5 but no BLC (CXCL13) or TECK (CCL25) as an active ingredient was prepared.

TABLE 5

| Ingredients | Preparation Example 7: BLC (CXCL13) (500 ng/ml) (wt %) | Preparation Example 8: TECK (CCL25) (500 ng/ml) (wt %) | Preparation Example 9: BLC (CXCL13) + TECK (CCL25) (500 ng/ml) (wt %) | Comparative Example 3 (wt %) |
|---|---|---|---|---|
| BLC (CXCL13)/ TECK (CCL25)/ BLC (CXCL13) + TECK (CCL25) | 0.01 | 0.01 | 0.01 | — |
| Amino acid stock | 0.05 | 0.05 | 0.05 | 0.05 |
| Mineral mixture | 0.0007 | 0.0007 | 0.0007 | 0.0007 |
| Glycerol | 3 | 3 | 3 | 3 |
| 1,3-Butylene glycol | 10 | 10 | 10 | 10 |
| Mineral oil | 5 | 5 | 5 | 5 |
| Cetyl alcohol | 2 | 2 | 2 | 2 |
| Xanthan gum | 0.5 | 0.5 | 0.5 | 0.5 |
| Purified water | Remainder | Remainder | Remainder | Remainder |

<Preparation Examples 10 to 12 and Comparative Example 4> Preparation of Creams Containing Chemokine Creams of Preparation Example 10, Preparation Example 11, and Preparation Example 12, respectively containing BLC (CXCL13), TECK (CCL25), and both BLC (CXCL13) and TECK (CCL25) as an active ingredient(s) and other ingredients at concentrations shown in the following Table 6, were prepared. Also, a cream of Comparative Example 4 containing ingredients at concentrations shown in the following Table 6 but no BLC (CXCL13) or TECK (CCL25) as an active ingredient was prepared.

TABLE 6

| Ingredients | Preparation Example 10: BLC (CXCL13) (500 ng/ml) (wt %) | Preparation Example 11: TECK (CCL25) (500 ng/ml) (wt %) | Preparation Example 12: BLC (CXCL13) + TECK (CCL25) (500 ng/ml) (wt %) | Comparative Example 4 (wt %) |
|---|---|---|---|---|
| BLC (CXCL13)/ TECK (CCL25)/ BLC (CXCL13) + TECK (CCL25) | 0.01 | 0.01 | 0.01 | — |
| Amino acid stock | 0.05 | 0.05 | 0.05 | 0.05 |
| Mineral mixture | 0.0007 | 0.0007 | 0.0007 | 0.0007 |
| Glycerol | 2 | 2 | 2 | 2 |
| Mineral oil | 10 | 10 | 10 | 10 |
| Olive emulsion wax | 3 | 3 | 3 | 3 |
| Cetyl alcohol | 2 | 2 | 2 | 2 |
| Purified water | Remainder | Remainder | Remainder | Remainder |

Detailed Description of Exemplary Embodiments

The present invention provides a cosmetic composition for skin improvement containing at least one chemokine selected from the group consisting of B lymphocyte chemoattractant (BLC) (also known as B cell-attracting chemokine 1 (BCA-1) or C-X-C motif ligand 13 (CXCL13)) and thymus-expressed chemokine (TECK) (also known as C-C motif ligand 25 (CCL25)) as an active ingredient.

The term "chemokine" used herein refers to a low-molecular-weight, basic heparin-binding protein directing leukocyte migration and activation. Each chemokine molecule has four cysteine residues, and the position of the first two cysteine residues is the factor that classifies chemokines into four subclasses such as the CXC family (CXCL), the CC family (CCL), the CX3C family (CX3CL), and the C family (XCL). Until now, more than 40 types of chemokines have been identified.

Among the chemokines, either one or both of BLC (CXCL13) and TECK (CCL25) are the active ingredients of the present invention.

The term "skin improvement" used herein may be interpreted to mean effects of skin regeneration, skin elasticity improvement, wrinkle prevention or improvement, skin moisturizing, skin whitening, anti-inflammation, and/or the like that can be induced by applying the active ingredient of the present invention to the skin.

The BLC or TECK may be used in combination with at least one polymer selected from the group consisting of alginates, collagens, hyaluronic acids, and gelatins, but the present invention is not limited thereto.

In one experimental example of the present invention, it was found that the expression of the Ki-67 marker (FIG. 5) and the rate of melanin reduction (FIG. 6) increased in a group treated with a BLC or TECK in alginate compared to an untreated group.

The BLC or TECK may be contained in a cosmetic composition in an amount of 0.0000001 to 10 parts by weight (1 ng/ml to 100 mg/ml) with respect to 100 parts by weight of the total weight of the cosmetic composition, but the present invention is not limited thereto.

The cosmetic composition may contain an adjuvant commonly used in cosmetics or dermatology, such as a fatty substance, an organic solvent, a solubilizer, a thickening agent, a gelling agent, a softening agent, an antioxidant, a suspending agent, a stabilizer, a foaming agent, a fragrance, a surfactant, water, an ionic or nonionic emulsifier, a filler, a sequestrant, a chelating agent, a preservative, a vitamin, a blocking agent, a wetting agent, an essential oil, a dye, a pigment, a hydrophilic or lipophilic active agent, lipid vesicles, or any other ingredient commonly used in cosmetic products. The adjuvant is included in the cosmetic composition in an amount commonly used in the cosmetics or dermatological field.

The cosmetic composition contains a cosmetically or dermatologically acceptable medium or base. The cosmetic composition may be provided in any form suitable for topical application; for example, the cosmetic composition may be in the form of a solution, a gel, a solid, a paste, a paste anhydrous product, an oil-in-water emulsion, a suspension, a microemulsion, microcapsules, microgranules, an ionic (liposome) or nonionic vesicular dispersion, a cream, a skin lotion, an emulsion, a powder, an ointment, a spray, or a stick-type concealer. The cosmetic composition may be prepared by a conventional method in the art. The cosmetic composition according to the present invention may alternatively be in the form of a foam or an aerosol composition further containing a compressed propellant.

The cosmetic composition containing an active ingredient(s) according to the present invention is not particularly limited in its formulation, and it may be formulated as a cosmetic product such as a softening toner, an astringent, a nourishing toner, a nourishing cream, a massage cream, a serum, an eye cream, an eye serum, a cleansing cream, a cleansing foam, a cleansing water, a beauty mask, a powder, a body lotion, a body cream, a body oil, or a body serum.

Alternatively, the cosmetic composition may be prepared into a formulation that can be applied to the skin, such as an absorbent gel, a pad, a patch, a sponge, or a mask pack, but the present invention is not limited thereto.

In each of Preparation Examples 1 to 12 of the present invention, a cosmetic composition containing BLC (CXCL13), TECK (CCL25), or both BLC (CXCL13) and TECK (CCL25) as an active ingredient(s) and formulated as a skin lotion, a serum, an emulsion, or a cream was prepared. When preparing a cosmetic composition containing both BLC (CXCL13) and TECK (CCL25) as active ingredients, the BLC (CXCL13) and TECK (CCL25) may be mixed according to an optimum blending ratio.

The above-described cosmetic composition may be applied topically or transdermally using microneedles or the like.

The cosmetic composition for skin improvement may be used for skin regeneration.

In one experimental example of the present invention, it was found that migration of keratinocytes was increased in a group treated with BLC (CXCL13) or TECK (CCL25), both of which are active ingredients used in the present invention, compared to the negative control (untreated group) and significantly increased compared to the positive control (group treated with stromal cell-derived factor-1α (SDF-1α), which is a cytokine) (FIG. 1). Also, the expression of proliferation marker Ki-67 (FIG. 3) and collagen IV (FIG. 4) was significantly increased by BLC (CXCL13) or TECK (CCL25) compared to the negative control (untreated group) and the positive control (group treated with SDF-1α). The results confirmed that the active ingredient of the present invention, BLC (CXCL13) or TECK (CCL25), had excellent effects on skin regeneration.

The cosmetic composition for skin improvement may be used for skin elasticity improvement.

In one experimental example of the present invention, it was found that use of cosmetic compositions of Preparation Examples 1 to 12 containing an active ingredient(s) of the present invention, BLC (CXCL13) and/or TECK (CCL25), resulted in greater skin elasticity improvement compared to use of cosmetic compositions of Comparative Examples 1 to 4 not containing the active ingredient; therefore, it was confirmed that the active ingredient of the present invention, BLC (CXCL13) or TECK (CCL25), had excellent effects on skin elasticity improvement.

The cosmetic composition for skin improvement may be used for wrinkle prevention or improvement.

In one experimental example of the present invention, it was found that use of cosmetic compositions of Preparation Examples 10 and 11 containing an active ingredient of the present invention, BLC (CXCL13) or TECK (CCL25), resulted in greater wrinkle improvement and better skin elasticity maintenance compared to use of the cosmetic composition of Comparative Example 4.

The cosmetic composition for skin improvement may be used for skin moisturization.

The cosmetic composition for skin improvement may be used for skin whitening.

In one experimental example of the present invention, it was found that the rate of melanin reduction was higher by 20 percentage points or more in a group treated with an active ingredient of the present invention, BLC (CXCL13) or TECK (CCL25) in alginate, compared to the negative control (untreated group); therefore, it was confirmed that the active ingredient of the present invention, BLC (CXCL13) or TECK (CCL25), had excellent effects on skin whitening (FIG. 6).

The cosmetic composition for skin improvement may be used for skin anti-inflammation.

In addition, the present invention provides a method for skin improvement that includes applying the cosmetic composition containing at least one active ingredient selected from the group consisting of BLC (CXCL13) and TECK (CCL25) to the skin for skin improvement.

Furthermore, the present invention provides use of BLC (CXCL13) and TECK (CCL25) for skin improvement.

It was confirmed that the active ingredient of the present invention, BLC (CXCL13) or TECK (CCL25), increased the expression of proliferation marker Ki-67 and collagen IV, which are proteins concerning skin regeneration and skin elasticity among cell-secreted substances derived from keratinocytes which play a key role in wound healing and skin regeneration, and exhibited an excellent wound-healing effect and the ability to induce chemotaxis of keratinocytes. Since BLC (CXCL13) and TECK (CCL25) have efficacy superior to that of SDF-1α which is a cytokine known to have a wound-healing effect, they can be continuously applied in a cosmetic composition for skin improvement.

INDUSTRIAL APPLICABILITY

Since the B lymphocyte chemoattractant (BLC) (also known as B cell-attracting chemokine 1 (BCA-1) or C-X-C motif ligand 13 (CXCL13)) and thymus-expressed chemokine (TECK) (also known as C-C motif ligand 25 (CCL25)) of the present invention increase the expression of proliferation marker Ki-67 and collagen IV which are proteins concerning skin regeneration and skin elasticity among keratinocyte-derived cell-secreted substances, have excellent melanin-reducing and wound-healing effects, and exhibit the ability to induce chemotaxis of keratinocytes, they can be applied in a cosmetic composition for skin improvement.

What is claimed is:

1. A method for skin improvement comprising applying a cosmetic composition comprising at least one active ingredient selected from the group consisting of a B lymphocyte chemoattractant (BLC) and a thymus-expressed chemokine (TECK) to skin for skin improvement.

2. The method of claim 1, wherein the cosmetic composition further comprises at least one polymer selected from the group consisting of alginates, collagens, hyaluronic acids, and gelatins.

3. The method of claim 1, wherein the cosmetic composition comprises the B lymphocyte chemoattractant (BLC) or thymus-expressed chemokine (TECK) in an amount of 0.0000001 to 10 parts by weight with respect to 100 parts by weight of a total weight of the cosmetic composition.

4. The method of claim 1, wherein said skin improvement is skin regeneration.

5. The method of claim 1, wherein the skin improvement is skin elasticity improvement.

6. The method of claim 1, wherein the skin improvement is wrinkle prevention or improvement.

7. The method of claim 1, wherein the skin improvement is skin moisturization.

8. The method of claim 1, wherein the skin improvement is skin whitening.

9. The method of claim 1, wherein the skin improvement is anti-inflammation.

* * * * *